US011576379B2

(12) United States Patent
Sherry et al.

(10) Patent No.: US 11,576,379 B2
(45) Date of Patent: Feb. 14, 2023

(54) ANTIMICROBIAL COMPOSITION COMPRISING ALKYLATED POLYVINYLPYRROLIDONE POLYMER

(71) Applicant: The Procter & Gamble Company, Cincinnati, OH (US)

(72) Inventors: Alan Edward Sherry, Newport, KY (US); Nicola John Policicchio, Mason, OH (US); Yuexi Wang, Cincinnati, OH (US); Francis Cornelio Ford, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/994,699

(22) Filed: Aug. 17, 2020

(65) Prior Publication Data
US 2021/0051957 A1 Feb. 25, 2021

(30) Foreign Application Priority Data
Aug. 20, 2019 (EP) .................... 19192578

(51) Int. Cl.
| A61L 2/18 | (2006.01) |
| C11D 1/66 | (2006.01) |
| C11D 1/72 | (2006.01) |
| C11D 1/825 | (2006.01) |
| C11D 11/00 | (2006.01) |
| C11D 17/04 | (2006.01) |
| C11D 3/37 | (2006.01) |
| C11D 3/43 | (2006.01) |
| C11D 3/48 | (2006.01) |
| A01N 25/34 | (2006.01) |
| A01N 33/12 | (2006.01) |
| A01N 43/36 | (2006.01) |
| A01N 47/44 | (2006.01) |
| A61L 2/26 | (2006.01) |
| A61L 101/32 | (2006.01) |

(52) U.S. Cl.
CPC ............ *A01N 43/36* (2013.01); *A01N 25/34* (2013.01); *A01N 33/12* (2013.01); *A01N 47/44* (2013.01); *A61L 2/18* (2013.01); *A61L 2/26* (2013.01); *C11D 1/825* (2013.01); *C11D 3/3776* (2013.01); *C11D 3/43* (2013.01); *C11D 3/48* (2013.01); *C11D 11/0023* (2013.01); *C11D 17/049* (2013.01); *A61L 2101/32* (2020.08); *C11D 1/662* (2013.01); *C11D 1/72* (2013.01)

(58) Field of Classification Search
CPC .............. A61Q 17/005; A01N 25/08

USPC ........................................ 424/401
See application file for complete search history.

(56) References Cited

U.S. PATENT DOCUMENTS

| 4,315,828 | A | 2/1982 | Church |
| 4,690,779 | A | 9/1987 | Baker et al. |
| 6,369,019 | B1* | 4/2002 | Gordon ................ C11D 3/2093 510/421 |
| 6,395,262 | B1* | 5/2002 | Favre ...................... A61Q 1/02 424/61 |
| 6,475,976 | B1 | 11/2002 | Mahieu et al. |
| 6,482,793 | B1 | 11/2002 | Gordon |
| 6,559,116 | B1* | 5/2003 | Godfroid ................. C11D 3/48 510/237 |
| 6,596,681 | B1 | 7/2003 | Mahieu et al. |
| 6,730,294 | B1 | 5/2004 | Kritzler |
| 7,704,935 | B1 | 4/2010 | Davis |
| 7,741,263 | B2 | 6/2010 | Kilkenny |
| 8,852,399 | B2 | 10/2014 | Neal et al. |
| 9,381,150 | B2* | 7/2016 | Cunningham ....... A61K 8/8182 |
| 2002/0183233 | A1* | 12/2002 | Mitra ..................... C11D 3/046 510/438 |
| 2003/0224030 | A1* | 12/2003 | Uchiyama ............ C11D 3/3765 424/405 |
| 2005/0124519 | A1 | 6/2005 | Sherry et al. |
| 2006/0165741 | A1* | 7/2006 | Coffindaffer ........... A61Q 19/00 424/401 |
| 2007/0011699 | A1 | 1/2007 | Kopra |
| 2007/0110699 | A1 | 5/2007 | Sherry |
| 2007/0129279 | A1 | 6/2007 | Sheirs et al. |
| 2007/0185004 | A1 | 8/2007 | Kilkenny |
| 2008/0124381 | A1* | 5/2008 | Barnhart ................ A61K 8/731 424/443 |
| 2011/0152925 | A1 | 6/2011 | Schorr |
| 2014/0135297 | A1 | 5/2014 | Narayanan |
| 2015/0202126 | A1 | 7/2015 | Graham |

FOREIGN PATENT DOCUMENTS

| EP | 3228689 A1 | 10/2017 |
| EP | 3263681 A1 | 1/2018 |
| EP | 3418363 A1 | 12/2018 |

OTHER PUBLICATIONS

Extended European Search Report; Application No. 19192578.3-1105; dated Feb. 17, 2020; 8 pages.

(Continued)

*Primary Examiner* — Walter E Webb
(74) *Attorney, Agent, or Firm* — Carolyn S. Powell; George H. Leal

(57) ABSTRACT

An antimicrobial composition comprising:
a) C2-C8 alkylated polyvinylpyrrolidone polymer; and
b) biocidal agent selected from the group consisting of quaternary ammonium compounds, chlorohexidine salts, polymeric biguanides, organic acids, hydrogen peroxide, tertiary alkyl amines, iodophors and mixtures thereof.

13 Claims, No Drawings

(56) References Cited

OTHER PUBLICATIONS

"Product guide Tomadol ethoxylated alcohols", Evonik, 2017, Retrieved from the Internet:URL:https://household-care.evonik.com/product/household-care/downloads/public/evonik%20-%20tomadol%20product%20guide.pdf[retrieved on Feb. 6, 2020].
"The HLB System a time-saving guide to emulsifier selection", Icl Americas Inc., Mar. 1980 (Mar. 1980), Retrieved from the Internet:URL:http://www.firp.ula.ve/archivos/historicos/76_Book_HLB_ICI.pdf[retrieved on Feb. 7, 2020].
Extended European Search Report; Application No. 19192589.0; dated Mar. 2, 2020; 17 pages.
Extended European Search Report; Application No. 19192593.2; dated Mar. 2, 2020; 13 pages.
U.S. Appl. No. 16/994,703, filed Aug. 17, 2020, Alan Edward Sherry, et al.
U.S. Appl. No. 16/994,706, filed Aug. 17, 2020, Alan Edward Sherry et al.
All Office Actions; U.S. Appl. No. 16/994,703.
All Office Actions; U.S. Appl. No. 16/994,706.
CM05118-WO-JC PCT Search Report and Written Opinion for PCT/US2020/070423 dated Nov. 12, 2020, 15 pages.

\* cited by examiner

ANTIMICROBIAL COMPOSITION COMPRISING ALKYLATED POLYVINYLPYRROLIDONE POLYMER

FIELD OF THE INVENTION

The present invention is in the field of antimicrobial compositions. In particular, it relates to a composition that provides surface sanitation, the composition comprises a hydrophobically modified polyvinylpyrrolidone polymer, and especially an alkylated polyvinylpyrrolidone polymer. The composition provides long-lasting antimicrobial benefits and good shine and it is well suited to be used on non-woven substrates.

BACKGROUND OF THE INVENTION

Compositions providing good and long-lasting antimicrobial benefits can leave streaks and marks, negatively impacting on the shine of the surface treated. Equally, compositions providing good shine do not seem good at providing antimicrobial benefits. Surfaces treated with some compositions can be left with a poor shine profile and a sticky/tacky surface that connotes lack of cleanliness to the user. This can be more acute with compositions that do not require rinsing.

Another challenge is to provide compositions that can be loaded on substrates, such as wipes to use as cleaning implements. Some compositions are either unsuitable to be keep on a substrate or adhere to the substrate too well and not to the surface to be cleaned.

Therefore, a need remains for a composition providing antimicrobial benefits, especially long-lasting antimicrobial benefits which at the same time does not leave visible residues on the surface and does not negatively affect the gloss and shine of the surface. There is also a need to provide a composition that is suitable to be used on substrates such as wipes.

SUMMARY OF THE INVENTION

According to the first aspect of the present invention, there is provided an antimicrobial composition. The composition comprises a C2-C8, preferably C2 to C6, more preferably C4 alkylated polyvinylpyrrolidone polymer and especially a butylated polyvinylpyrrolidone polymer. The polymer is sometimes referred herein to as "the polymer of the invention". The composition also comprises a biocidal agent. The biocidal agent is selected from the group consisting of quaternary ammonium compounds, chlorohexidine salts, preferably chlorohexidine diacetate, polymeric biaguanides, preferably polyhexamethylene biguanide, organic acids, hydrogen peroxide, tertiary alkyl amines, iodophors and mixtures thereof. Preferably, the biocidal agent comprises a chlorohexidine salt or a combination of a chlorhexidine salt and a quaternary ammonium compound. Consequently, the most preferred compositions comprise a butylated polyvinylpyrrolidone polymer, chlorohexidine diacetate and optionally one or more quaternary ammonium compounds.

According to the second aspect of the invention there is provided an article treated with the composition of the first aspect of the invention. The article is preferably in the form of any disposable or partially reusable substrate comprising one or more nonwoven layers. The article provides residual antimicrobial and self-sanitizing properties to a surface treated with it. The article is sometimes herein referred to as "the article of the invention".

According to the third aspect of the invention there is provided a method of treating a surface, preferably a hard surface, the method provides antimicrobial benefits, sanitization and shine to the treated surface. The method comprises the steps of: optionally pre-cleaning the surface to be treated and treating the surface with the composition or the article of the invention.

According to the fourth aspect of the invention there is provided the use of the composition or article of the invention to provide residual self-sanitizer efficacy and shine to a surface.

The elements of the composition of the invention described in relation to the first aspect of the invention apply mutatis mutandis to the other aspects of the invention.

DETAILED DESCRIPTION OF THE INVENTION

The present invention encompasses an antimicrobial composition. The composition comprises an alkylated polyvinylpyrrolidone polymer, preferably a C2-C6 alkylated polyvinylpyrrolidone polymer, more preferably a C4 alkylated polyvinylpyrrolidone, especially butylated polyvinylpyrrolidone, a biocidal agent, preferably a chlorohexidine salt, more preferably chlorohexidine diacetate, optionally but preferably a quaternary ammonium compound, a non-ionic surfactant, a solvent and a carrier. Preferably the composition provides fast sanitization. Preferably the composition also provides residual sanitization (i.e., long lasting sanitization).

There is also provided an article, preferably in the form of a disposable or partially reusable substrate comprising one or more nonwoven layers, preferably a wipe. The article is impregnated with the composition of the invention. There is also provided a canister comprising the article. There is also provided a method of sanitizing using the composition or the article of the invention and the use of the composition of the invention to provide good shine, fast and long-lasting sanitization to a surface, preferably a hard surface.

All percentages, ratios and proportions used herein are by weight percent of the composition, unless otherwise specified. All average values are calculated "by weight" of the composition, unless otherwise expressly indicated. All ratios are calculated as a weight/weight level, unless otherwise specified.

All measurements are performed at 25° C. unless otherwise specified.

Unless otherwise noted, all component or composition levels are in reference to the active portion of that component or composition, and are exclusive of impurities, for example, residual solvents or by-products, which may be present in commercially available sources of such components or compositions.

As used herein, the terms "microbe" or "microbial" should be interpreted to refer to any of the microscopic organisms studied by microbiologists or found in the use environment of a treated surface. Such organisms include, but are not limited to, bacteria and fungi as well as other single-celled organisms such as mould, mildew and algae. Viruses (enveloped and non-enveloped) and other infectious agents are also included in the term microbe.

"Antimicrobial" further should be understood to encompass both microbiocidal and microbiostatic properties. That is, the term includes microbe killing, leading to a reduction in number of microbes, as well as a retarding effect of microbial growth, wherein numbers may remain more or less constant (but nonetheless allowing for slight increase/ decrease). By "sanitizing composition" is herein meant a composition that provides 99.9% kill of microorganisms.

By "residual self-sanitizing (RSS) composition" is herein meant a composition that after treating a surface still keeps killing microorganisms placed on the treated surface for at least 12 hours, more preferably at least 24 hours.

By "quick kill" or "fast sanitization" is herein meant a composition that provides sanitizing activity benefits within a time period ranging from about 30 seconds to about 5 minutes.

For ease of discussion, this description uses the term antimicrobial to denote a broad-spectrum activity (e.g. against bacteria and fungi, or against bacteria and viruses). When speaking of efficacy against a particular microorganism or taxonomic rank, the more focused term will be used (e.g. antifungal to denote efficacy against fungal growth in particular). Using the above example, it should be understood that efficacy against fungi does not in any way preclude the possibility that the same antimicrobial composition may demonstrate efficacy against another class of microbes.

Antimicrobial Composition

The composition of the invention is preferably in aqueous liquid form and provides immediate antimicrobial benefits as well as and self-sanitizing longer lasting sanitizing properties. The composition comprises a polyvinylpyrrolidone polymer that is hydrophobically modified via alkylation. The composition preferably comprises a C2 to C8 alkylated polyvinylpyrrolidone polymer, more preferably a butylated polyvinylpyrrolidone polymer, and a biocidal agent, preferably a chlorohexidine salt, more preferably chlorohexidine diacetate. The composition further comprises a carrier (such as water and/or a mixture of water and lower molecular weight alcohol), a surfactant, a solvent, an anti-foam agent and a fragrance, among other components.

The composition can be applied to a surface by spraying, rolling, fogging, wiping or other means. Once dry, the liquid formulation leaves a residual protective film on the surface. The residual film includes an embedded biocide which is believed to provide surface protection against microbial contamination for an extended time period following its application. The disinfectant composition imparts a film with the capacity to quickly kill bacteria and other germs for at least 12 hours, more preferably at least 24 hours after deposition of the film on the treated surface. The film will remain on the surface and is durable to multiple touches and wearing of the surface. Following application of the composition and drying, the treated surface has a good shine profile.

The composition of the invention is suited to treat any type of surfaces but it is more suited to treat hard surfaces, such as those found in private households, as well as in commercial, institutional and industrial settings. Surfaces to be treated include kitchen and bathroom surfaces, e.g., floors, walls, tiles, windows, cupboards, countertops, tables, sinks, showers, shower plastified curtains, wash basins, WCs, fixtures and fittings and the like made of different materials like ceramic, vinyl, no-wax vinyl, linoleum, melamine, glass, steel, kitchen work surfaces, any plastics, plastified wood, metal or any painted or varnished or sealed surface and the like. Hard surfaces also include household or commercial appliances including, but not limited to refrigerators, freezers, washing machines, automatic dryers, ovens, microwave ovens, dishwashers and so on.

In a preferred embodiment, the liquid composition herein is an aqueous compositions. Such composition comprises from 30% to 99.5% water by weight of the total composition, preferably from 50% to 99% and more preferably from 80% to 98.5%.

At the point of use, the composition of the present invention preferably has a viscosity from about 1 cps to about 300 cps when measured at 20° C. with an AD1000 Advanced Rheometer from Atlas® shear rate 10 s$^{-1}$ with a coned spindle of 40 mm with a cone angle 2° and a truncation of ±60 μm. It will be appreciated that concentrated variants may have a viscosity greater than 300 cps, but that the viscosity in most cases will fall between 1 and 300 cps when the concentrate is diluted prior to use.

The composition of the invention is well suited to be impregnated on a nonwoven substrate.

The composition of the invention might be obtained by diluting with water a concentrated solution.

Alkylated Polyvinylpyrrolidone Polymer

Without wishing to be bound by theory, it is believed that to provide long-lasting disinfection and at the same time leave the cleaned surface free of streaks, the polymer should display water barrier properties so as to resist re-dissolution in water and deliver a clear coat film upon drying. Preferably, the dried-on polymer film has limited stickiness. The polymer of the invention is hydrophobically modified, and preferably comprises C2-C8 alkylated polyvinylpyrrolidone polymer, especially butylated polyvinylpyrrolidone. The hydrophobic character of the polymer means that it withstands water and moisture treatments and is more difficult to rub away. The polymer is also believed to interact, shield or protect biocidal active present in the composition, thereby preventing the biocide from being easily washed or rubbed away. In this manner, enhanced residual antimicrobial activity is achieved.

The polymer preferably has a molecular weight of from about 5,000 to about 40,000 g/mol, more preferably from about 10,000 to about 20,000 g/mol, even more preferably from about 12,000 to about 18,000 g/mol. The preferred polymer for use herein is a butylated polyvinylpyrrolidone with a molecular weight of from about 12,000 to about 18,000 g/mol. The polymer is present in sufficient amount to immobilize the biocidal agent following the dry down process, preferably the composition comprises from about 0.05% to 2.0%, more preferably from 0.10% to 1.5% and most preferably from about 0.2% to 1.0% by weight of the composition of polymer. Higher levels (e.g., 0.25% to 1.5%) may be needed in compositions embedded in premoistened wipes whereas lower levels (e.g., 0.10% to 0.75%) may be sufficient for use in ready-to-use spray products. Differences in polymer level stem from the fact that premoistened wipes deliver less solution on surface than what is typically provided by a trigger sprayer.

The ratio of vinylpyrrolidone to alkyl groups in the alkylated polyvinylpyrrolidone is typically from 20:80 to about 95:5, more preferably from about 80:20 about 90:10. The Antaron® and Ganex® tradenames are used to designate alkylated polyvinylpyrrolidone polymers supplied by Ashland. Butylated polyvinylpyrrolidone polymer designated as Ganex P-904 LC is particularly suitable for use in the present invention.

Biocidal Agent

The biocidal agent needs only be present in germicidally effective amounts, which can be as little as 0.01% by weight of the composition. Preferably, the composition of the invention comprises the biocidal agent at an active level of from 0.02% to 2.0%, more preferably from 0.05% to 1.6%, still more preferably from 0.1% to 1.2%, and most preferably from 0.20% to 1.0% by weight of the composition. A germicidally effective amount of the biocidal agent can be considered to result in at least a log 3.0 reduction of bacteria, fungi or viruses using the US EPA Germicidal Spray Test or EPA wipe method (protocol #01-1A) with a contact time in the range of 30 seconds to 10 minutes, more preferably 30 seconds to 5 minutes.

Suitable quaternary ammonium compounds are those of the formula:

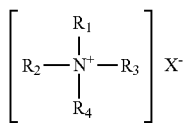

wherein at least one of R1, R2, R3 and R4 is an aliphatic or aryl aliphatic hydrophobic group comprising from 6 to 26 carbon atoms, and the entire cation portion of the molecule has a molecular weight of at least 165. The hydrophobic radicals may be long-chain alkyl, long-chain alkoxy aryl, long-chain alkyl aryl, halogen-substituted long-chain alkyl aryl, long-chain alkyl phenoxy alkyl, aryl alkyl, etc. The R1, R2, R3 and R4 groups may be straight chained or may be branched, but are preferably straight chained, and may include one or more amide or ester linkages. X is a counterion that can be a halide (e.g., chloride, bromide iodide), or X can be a methosulfate anion, or X can be a carbonate or bicarbonate ion.

Exemplary quaternary ammonium compounds include the monoalkyl trimethyl ammonium halides such as cetyl trimethyl ammonium bromide, alkyl aryl ammonium halides such as octadecyl dimethyl benzyl ammonium bromide, N-alkyl pyridinium halides such as N-cetyl pyridinium bromide, and the like. Other suitable types of quaternary ammonium compounds include octyl phenoxy ethoxy ethyl dimethyl benzyl ammonium chloride, N-(laurylcocoaminoformylmethyl)-pyridinium chloride, and the like.

More preferred quaternary ammonium compounds used in the compositions of the invention include those of the structural formula:

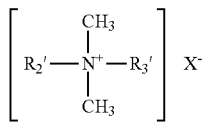

wherein R2' and R3' may be the same or different and are selected from C8-C12 alkyl, or R2' is C12-C16 alkyl, C8-C18 alkylethoxy, C8-C18 alkylphenolethoxy and R3' is benzyl, and X is a halide, for example a chloride, bromide or iodide, or X is a methosulfate counterion, or X is a bicarbonate/carbonate counterion. The alkyl groups recited in R2' and R3' may be linear or branched, but are preferably substantially linear, or fully linear.

Particularly useful commercially available quaternary germicides include raw materials sold under the tradenames Bardac, Carboquat and Barquat. These quaternary ammonium compounds are usually provided in a solvent, such as a C2 to C6 alcohol (such as ethanol, n-propanol, isopropanol, n-butanol, sec-butanol, and the like), glycols such as propylene glycol or glycerin, or in water, or mixtures containing water, such alcohols, and such glycols. In one embodiment, the quaternary ammonium compound is didecyl dimethyl ammonium bicarbonate/carbonate or a didecyl dimethyl ammonium chloride, such as supplied by Lonza under tradenames such as Carboquat H™, Carboquat MW-50™, Bardac 2250, Bardac 2270™, Bardac 2270E™ and Bardac 228™. In another embodiment the quaternary ammonium compound comprises a blend of alkyl, preferably C12-C18, dimethyl benzyl ammonium chloride compounds such as supplied by Lonza and Stepan under the trade names Bardac LB-80™ and BTC 8358™, respectively. In another embodiment, the quaternary ammonium compound comprises a blend of alkyl, preferably C12-C18, dimethyl benzyl ammonium chloride and alkyl, preferably C12-C18, dimethyl ethylbenzyl ammonium chloride, such as supplied by Lonza and Stepan under the trade names Barquat 4280Z™ and BTC 2125M™, respectively. In still another embodiment, the quaternary ammonium compound comprises a didecyl dimethyl ammonium quaternary compound (counterion can be chloride, bromide, bicarbonate, carbonate or mixtures thereof) and a blend of alkyl, preferably C12-C18 alkyldimethylbenzyl ammonium quaternary compounds (counterions can be chloride, bromide, bicarbonate, carbonate or mixtures thereof); such materials are available under the trade names Bardac 205M™ and Bardac 208M™ from Lonza.

In one preferred embodiment, the antimicrobial agent comprises a mixture of didecyl dimethyl ammonium bicarbonate/carbonate (e.g., trade name Carboquat) together with a chlorhexidine salt (e.g., chlorhexidine diacetate) and optionally further comprises a gluconate or glycolate salt (e.g., sodium, potassium, ammonium and the like), or either gluconic acid or glycolic acid (used especially if composition pH is above 8) such that the pH of the final composition is from about pH 5 to about pH 8. It is found that quaternary ammonium halide compounds (i.e., those comprising chloride or bromide counterions) can precipitate chlorhexidine diacetate at very low temperatures such as encountered when freezing (e.g., −18° C.) then thawing (e.g., +20° C. to +25° C.) solutions or wipes impregnated with solution comprising both quaternary ammonium compound and chlorhexidine compound. The use of the quaternary ammonium compound with bicarbonate ion, is found to remedy the issue. In cases where there is less concern about precipitation from extremely low temperatures, the antimicrobial agent preferably consist of a combination of quaternary ammonium halide compound or mixture of compounds, and a chlorhexidine salt compound.

Chlorohexidine Salt

Chlorhexidine salts include chlorhexidine digluconate, chlorhexidine dihydrochloride, chlorhexidine bis-bicarbonate, chlorhexidine carbonate or chlorhexidine diacetate. Chlorhexidine diacetate is especially preferred for use herein. Chlorhexidine diaceate has relatively low solubility in water (i.e., ~1% in water) and is slow to solubilize, which makes it an ideal for residual sanitizer applications. It is also cidally effective at low concentrations. Additionally, since chlorhexidine diacetate is a salt, it has little or no effect on the filming or streaking profile of the inventive composition. In one embodiment, chlorhexidine diacetate is used as the only antimicrobial active in the composition; in another embodiment, it is present as one of multiple registered actives in the composition.

Polymeric Biguanide

The polymeric biguanide may comprise polyhexamethylene biguanide (PHMB), polyhexamethylene monoguanide (PHMG), polyethylene biguanide (PEB), polytetramethylene biguanide (PTMB), polyhexamethylene biguanide (PHMB), polymethylene biguanide (PMB), poly(allylbiguanidinio-co-allyamine, poly(N-vinyl-biguanide), poly allylbiguanide etc. Preferred polymeric biguanide for use herein is a polyalkylene biguanide, more preferably polyhexamethylene biguanide hydrochloride with an average of repeating biguanide units between 10 and 50 or from 10 to 25. Such polyhexamethylene biguanide is supplied as a 20% solution in water and sold for multiple applications by Lonza under variants of the tradename Vantocil (e.g., Vantocil IB, Vantocil P, etc.) as well as under the tradename Reputex.

Organic Acids

Preferred organic acid for use herein includes citric acid, glycolic acid, lactic acid, octanoic acid, nonanoic acid, decanoic acid, hypochlorous acid and mixtures thereof. The organic acids can be oligomeric or polymeric. For example, polyacrylic acid of molecular from 500 to 100,000, polymaleic acid of molecular weight from 250 to 5,000 and copolymers comprising acrylic and maleic monomer units wherein the copolymer has a molecular weight from 1,000 to 50,000 are suitable organic acids.

Hydrogen Peroxide

Hydrogen peroxide can also be used as a biocidal agent. Without wishing to be limited by theory, it is believed that hydrogen peroxide will form a stabilizing complex with hydrophobically modified polyvinylpyrrolidones of the invention. Such a complex may limit loss of hydrogen peroxide on evaporation, and strengthen the composition antimicrobial properties, including residual antimicrobial properties.

Tertiary Alkyl Amine

A tertiary alkyl amine, such as an alkyl amine having from about 8 to about 16 carbon atoms. Examples of amine biocides that may be used in the composition include N,N-bis(3-aminopropyl) dodecylamine, N-(3-aminopropyl)-N-dodecylpropane-1,3-diamine, N-(3-aminopropyl)-N-decyl-1,3-propanediamine, N-(3-aminopropyl)-N-tetradecyl-1,3-propanediamine, or mixtures thereof.

Iodophors

An iodophor is a preparation containing iodine complexed with a solubilizing agent. Iodophors may be formed by complexation of iodine (e.g., Betadine/povidone-iodine) with non-ionic surfactant or complexation with polyvinylpyrrolidone. Without wishing to be limited by theory, it is believed that hydrogen peroxide will also form a stabilizing complex with a hydrophobically modified polyvinylpyrrolidone. Such a complex may limit loss of iodine on evaporation, and strengthen the composition antimicrobial properties.

Non-Ionic Surfactants

Preferred nonionic surfactants are ethoxylate surfactants that include alcohol ethoxylate surfactants, polyethylene glycols, ethoxylated polyols esterified with fatty acids and mixtures thereof. The non-ionic surfactant provides surface tension lowering properties, surface wetting and some cleaning, and is preferably present at a level from about 0.01% to 1.0%, more preferably from about 0.03% to about 0.50%, still more preferably from about 0.04% to about 0.30%, and most preferably from about 0.05% to about 0.25% by weight of the composition.

Alcohol ethoxylate surfactants suitable for use herein have the formula:

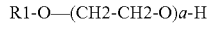

R1-O—(CH2-CH2-O)$a$-H wherein R1 is a linear or branched C6 to C20 alkyl, preferably linear or branched C8 to C18 alkyl, more preferably linear or branched C9 to C16 alkyl; a is an integer from 2 to 60, preferably from 4 to 30, more preferably from 5 to 25 most preferably from 5 to 18.

Polyethylene Glycols

Polyethylene glycols are suitable nonionic compounds for use herein, in particular polyethylene glycol compounds with a molecular weight between 400 and 40,000, more preferably between 800 and 20,000.

Ethoxylated Polyols Esterified with Fatty Acids

Preferred ethoxylated polyols esterified with fatty acids include polysorbate-type nonionic surfactant formed by the ethoxylation of sorbitan followed by addition of fatty acid. Suitable fatty acids include lauric, palmitic, stearic, oleic acid and mixtures thereof. Preferred for use herein are polyoxyethylene (20) sorbitan monolaurate, polyoxyethylene (20) sorbitan monopalmitate, polyoxyethylene (40) sorbitan monopalmitate, and mixtures thereof. Especially suitable for use herein is polyoxyethylene (20) sorbitan monolaurate.

Preferred for use herein is a nonionic ethoxylate system with an average HLB value greater than 13, more preferably an average HLB value from about 14 to about 18, wherein HLB value is computed according to the equation HLB=20*$M_h$/M where $M_h$ is the molecular mass of the ethoxylate portion of the molecule and M is the molecular mass of the whole molecule.

Examples of commercially available nonionic ethoxylates suitable for use herein includes PEG 8000 (HLB=20) from Dow, sorbitan monolaurate PEG 20 (AKA Tween 20, HLB=16.7) from Croda, and Emulan T3070 (C13 EO30 HLB=17) from BASF.

Anionic Surfactant

Many biocidal agents, including quaternary ammonium compounds, chlorhexidine compounds, polybiguanide compounds and tertiary amines, will typically interact with anionic surfactants, resulting in less antimicrobial efficacy and more residue on the treated surface (and hence less shine). When such antimicrobial actives are present, the composition of the invention preferably comprises limited amounts, or no anionic surfactant, with the exception of polycarboxylated anionic surfactants.

If the antimicrobial composition comprises anionic surfactant, other than polycarboxylated anionic surfactant, at a level of up to 2.0 wt %, preferably up to 1.0 wt %, or up to 0.1 wt % of anionic surfactant. In most preferred embodiments, the composition is substantially free, or completely free, of anionic surfactant other than polycarboxylated anionic surfactant.

Suitable polyalkoxylate polycarboxylates surfactant can have the empirical formula:

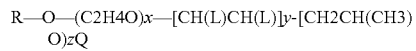

R—O—(C2H4O)$x$—[CH(L)CH(L)]$y$-[CH2CH(CH3)O]$z$Q wherein R is a hydrocarbon hydrophobic group, preferably alkyl, containing from 6 to 16, preferably from 8 to 14 carbon atoms; x is a number from 0 to 60, preferably from 4 to 50, more preferably from 6 to 50; L is either a C1-3 alkyl group or a group having the formula —CH—(COO—)CH2(COO—), with at least one L group in each molecule being —CH(COO—)CH2(COO—); y is a number from 1 to 12, preferably from 2 to 10, more preferably from 3 to 8; z is a number from 0 to 20, preferably from 0 to 15, more preferably from 0 to 10; and Q is selected from the group consisting of H and sulfonate groups, the compound being rendered electrically neutral by the presence of cationic groups, preferably selected from the group consisting of sodium, potassium, and substituted ammonium, e.g., monoethanol ammonium, cations. Specific examples of such polyalkoxylate polycarboxylate surfactant include the following: Poly-Tergent® C9-51B (CS-1) (x=12; y=8; and Z=17); Poly-Tergent® C9-62P (x=4; y=3; and z=17); Poly- Tergent C9-74P (x=10; y=3.5; and Z=3.5); and Poly-Tergent C9-92 (x=approximately 55; y=6.5; and z=0). R is believed to be an alkyl group such as a linear C9 alkyl group, and Q is believed to be H. The Poly-Tergent® surfactants are now sold under the Plurafac® trade name by BASF.

Suitable polycarboxylated anionic surfactants include alkoxylated polymer, alkyl ether, alkenedioic acid salts, for instance, as sold those under the Plurafac™ CS-10 tradename by BASF.

For compositions that leverage the antimicrobial properties of organic acids, hydrogen peroxide and iodofors, a wider selection of anionic surfactants can be used, including C8-C18 alkyl sulfate, C8-C18 alkyl ethoxy sulfate, dodecyl benzene sulfonate, C14-C17 paraffin sulfonate, C8-C18 alkyl carboxylates, C8-C18 ethoxy carboxylates, and the like. These anionic surfactants can be found in McCutcheon's Detergents and Emulsifiers, North American Ed. 2018, incorporated herein by reference. The hard surface cleaning composition can comprise from about 0.01% to about 1.0%, more preferably from about 0.03% to about 0.50%, by weight of anionic surfactant.

Additional Surfactant:

The composition of the invention may comprise additional surfactant, preferably selected from: an amphoteric, zwitterionic, and mixtures thereof. The antimicrobial composition can comprise from about 0.01% to about 1.0%, more preferably from about 0.03% to about 0.50% by weight of the additional surfactant.

Other Ingredients

Thickener: The composition of the invention can comprise a thickener.

Suitable thickeners include polyacrylate based polymers, preferably hydrophobically modified polyacrylate polymers; hydroxyl ethyl cellulose, preferably hydrophobically modified hydroxyl ethyl cellulose, xanthan gum, and mixtures thereof. Xanthan gum is one suitable thickener used herein. Xanthan gum is a polysaccharide commonly used rheology modifier and stabilizer. Suitable Xanthan gum is commercially available under trade name Kelzan T® from CP Kelco.

When used, the antimicrobial liquid hard surface cleaning composition comprises from 0.1% to 3% by weight of the total composition thickener, preferably from 0.2% to 2%, more preferably most preferably from 0.25% to 1%.

Chelating agent: The composition of the invention can comprise a chelating agent or crystal growth inhibitor. A preferred biodegradable chelating agent of use herein is ethylene diamine N,N'-disuccinic acid, or alkali metal, or alkaline earth, ammonium or substitutes ammonium salts thereof or mixtures thereof. Ethylenediamine N,N'-disuccinic acids is, for instance, commercially available under the tradename (S,S)EDDS® from Palmer Research Laboratories. Most preferred biodegradable chelating agent is L-glutamic acid N,N-diacetic acid (GLDA) commercially available under tradename Dissolvine 47S from Akzo Nobel.

Suitable amino carboxylates of use herein include ethylene diamine tetra acetates, diethylene triamine pentaacetates, diethylene triamine pentaacetate (DTPA), N-hydroxyethylethylenediamine triacetates, nitrilotriacetates, ethylenediamine tetrapropionates, triethylenetetraamine-hexa-acetates, ethanoldiglycines, and methyl glycine diacetic acid (MGDA), both in their acid form, or in their alkali metal, ammonium, and substituted ammonium salt forms. Particularly suitable amino carboxylate to be used herein is propylene diamine tetra acetic acid (PDTA) which is, for instance, commercially available from BASF under the trade name Trilon FS® and methyl glycine di-acetic acid (MGDA). Most preferred aminocarboxylate used herein is diethylene triamine pentaacetate (DTPA) from BASF. Other carboxylate chelating agents of use herein include salicylic acid, aspartic acid, glutamic acid, glycine, malonic acid or mixtures thereof.

Cleaning polymer: The antimicrobial composition may comprise a cleaning polymer. The polymer can be selected from the group consisting of: a vinylpyrrolidone homopolymer (PVP); a polyethyleneglycol dimethylether (DM-PEG); a vinylpyrrolidone/dialkylaminoalkyl acrylate or methacrylate copolymers; a polystyrenesulphonate polymer (PSS); a polyvinyl pyridine-N-oxide (PVNO); a polyvinylpyrrolidone/vinylimidazole copolymer (PVP-VI); a polyvinylpyrrolidone/polyacrylic acid copolymer (PVP-AA); a polyvinylpyrrolidone/vinylacetate copolymer (PVP-VA); a polyacrylic polymer or polyacrylic-maleic copolymer; and a polyacrylic or polyacrylic maleic phosphono end group copolymer; a polyethyleneimine polymer such as carboxylated polyethyleineimine; and mixtures thereof.

The composition optionally though preferably comprises a soil entrainment polymer to aid in removal of particulate soils from hard surfaces. The entrainment polymer has a molecular weight from about 50,000 to about 10,000,000, more preferably from about 100,000 to about 8,000,000. Examples of such polymers for use in hard surface cleaning applications are disclosed in U.S. Pat. Nos. 6,653,274 and 8,568,702 (herein incorporated by reference). The entrainment polymer is a flocculating or coagulating polymer, and has high affinity for cellulosic fibres typically used in cleaning implements (e.g., paper towels, newspapers, pre-moistened wipes). Such properties drive the soil removal process and limit re-deposition. Preferred polymers are either highly ethoxylated materials or highly charged materials. Non-limiting examples of suitable soil entrainment polymers include Hyperfloc NE823F, Hyperfloc ND823 A from Hychem, Mirapol Surf S-100 and Mirapol HSC 300 from Solvay, and Lupasol SK from BASF. A particular preferred entrainment polymer for use in this invention combines high molecular weight (Mw>500,000) together with both positively charged and negatively charged monomers and has the chemical structure:

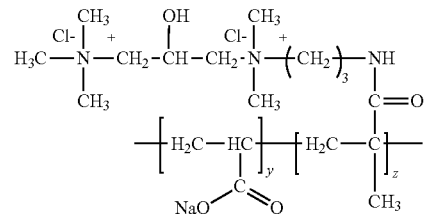

wherein the weight ratio y/z is from about 1:5 to about 5:1, more preferably y/z 2:1. This polymer displays a high affinity for particulate soils and hydrophilic fibres, and additionally can enhance the wetting properties of the overall composition. Mirapol HSC 300, available from Solvay, is a commercial source of this type of polymer.

If present, the soil entrainment polymer comprises less than 0.2% by weight of the overall composition. More preferably the soil entrainment polymer or mixture of polymers) comprises from about 0.002% to about 0.15% and most preferably from about 0.005% to about 0.10% or from about 0.01% to about 0.05% by weight of the overall composition at the point of use.

Solvents:

The composition herein can advantageously include solvents for perfume/fragrance dissolution as well as to enhance surface wetting and cleaning. It is found isopropanol and ethanol, most preferably ethanol can help fragrance dissolution and character even at solvents levels as low as 0.25%. Glycol ethers such as propylene glycol n-butyl ether are also suitable solvents for use herein. Additionally, benzyl alcohol and 3-hydrobutyl butyrate available from Eastman can advantageously be used to strengthen the overall composition wetting and cleaning properties.

When present, the level solvent is preferably from about 0.10% to about 5%, more preferably from about 0.25% to about 3% by weight of the overall composition.

Solfactants: The antimicrobial liquid composition may comprise solfactants, i.e. compounds having efficacy as both solvents and surfactants. Suitable solfactants include but are not limited to glycerin ether ethoxylate solfactants of the formula:

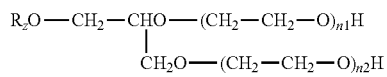

wherein $R_z$ is a linear or branched alkyl group having 1 to 30 carbon atoms, wherein $n_1$ and/or $n_2$ is 1 to 20. Suitable solfactants are described in US 2014/0005273 A1.

Perfumes: The liquid hard surface cleaning compositions preferably comprise a perfume. Suitable perfumes provide an olfactory aesthetic benefit and/or mask any "chemical" odour that the product may have.

Other optional ingredients: The composition of the invention may comprise a variety of other optional ingredients depending on the technical benefit aimed for and the surface treated. Suitable optional ingredients of use herein include builders, other polymers, buffers, bactericides, hydrotropes, colorants, stabilisers, radical scavengers, abrasives, soil suspenders, anti-dusting agents, dispersants, anti-foam agents, pigments, silicones and/or dyes.

A preferred composition of the invention comprises:
a) from 0.05% to 2% by weight of the composition of the polymer, preferably C2-C8 alkylated polyvinylpyrrolidone, more preferably butylated polyvinylpirrolidone;
b) from 0.05% to 2% by weight of the composition of the biocidal agent wherein the biocidal agent comprises a chlorhexidine compound, preferably chlorohexidine diacetate;
c) optionally but preferably from 0.01% to 1% by weight of the composition of a non-ionic ethoxylate surfactant, preferably a non-ionic ethoxylate surfactant, more preferably a mixture of an alcohol ethoxylate surfactant and a polyoxyethylene (20) sorbitan monolaurate; and
d) optionally but preferably from 0.05% to 50% by weight of the composition of a solvent selected from the group consisting of C2 to C4 alcohols, glycol ethers, and mixtures thereof, preferably ethanol, isopropanol or propylene glycol n-butyl ether, especially preferred propylene glycol n-butyl ether.

Wipe or Pad:

The composition can also be comprised in an article of manufacture. For instance, the composition can be comprised in a spray dispenser, preferably the composition is in a substrate such as a wipe or pad. The wipe or pad can be a single layer substrate or a multilayered substrate wherein the layers are bonded together by chemical or thermal means. The wipe or pad can be impregnated with the composition of the invention at the point of use or can be supplied as a pre-moistened substrate. Suitable fibrous wipes can comprise synthetic and natural, or natural derived fibres. Suitable natural fibres include cellulose as well as modified and regenerated cellulose fibres such as rayon (including Lyocell fibres), as well as fibres derived from lactic acid (e.g., polylactic acid or PLA). Suitable synthetic fibres include polyethylene, polypropylene, polyester, polyamide, and the like. Polymeric fibres can be spun-bonded to form the wipe. Suitable pads include foams and the like, such as HIPE-derived hydrophilic, polymeric foam.

Method of Sanitizing a Surface:

The compositions described herein are particularly suited for disinfecting hard and soft surfaces selected from the group consisting of: glazed or non-glazed ceramic tiles, enamel, stainless steel, Inox®, Formica®, vinyl, no-wax vinyl, linoleum, melamine, glass, plastics and plastified wood, painted surfaces, cloths, concrete, ceramic or no-wax vinyl floors, fabrics, leather and vegan leather, and combinations thereof.

The compositions used herein can be used in domestic and institutional settings.

For general disinfection and residual-self-sanitization, especially of kitchen surfaces, bathroom surfaces, tables and other surfaces in homes are institutions, and the like, the preferred method of cleaning comprises the step of:
(a) optionally pre-cleaning the surface to be treated; and
(b) applying the sanitizing composition to said surface.

a) Optional pre-cleaning step for tough soil removal

The optional pre-cleaning step may be beneficial for removal of highly tenacious or tough to clean soil. While not wishing to be limited by theory, it is believed that the polymer of the invention protects the surface from microbial contamination by forming a film that imparts moisture and wear resistance properties on said surface. The barrier film, which also comprises biocidal active, thus provides continuous self-sanitizing properties against microbes that may be introduced on the surface. It is believed that deposition of the protective antimicrobial polymer film can compete with the cleaning properties of optional surfactants that may be included in the composition. The degree to which this can happen is dependent on the level of polymer and the types and levels of surfactant present in the composition, as well as on the tenacity of soils on the hard surface to be cleaned prior to application of the antimicrobial composition of the invention.

(b) applying the sanitizing composition using concentrates, ready-to-use liquids and pre-moistened wipes If desired, the sanitizing liquid composition can be a concentrate that is diluted at the point of use. The concentrate may be diluted before application, for instance, to a level of from 1% to 20%, or from 5% to 10% by volume. The specifics for product dilution will depend upon initial product concentration, desired application use and desired speed of antimicrobial activity. In preferred embodiments, the liquid hard surface cleaning composition is diluted with water.

The dilution level is expressed as a percent defined as the fraction of the liquid hard surface cleaning composition, by volume, with respect to the total amount of the diluted composition. For example, a dilution level of 5% by volume is equivalent to 50 ml of the liquid hard surface cleaning composition being diluted to form 1000 ml of diluted composition. The diluted composition can be applied by any suitable means, including using a mop, sponge, wipe, paper towel or other suitable implement. The hard surface may be rinsed, preferably with clean water, in an optional further step, and also as a further step, wiped, such as with a cloth or paper towel.

In another preferred embodiment said method of sanitizing a hard surface includes the steps of applying, preferably spraying, a ready to use liquid composition onto said surface, leaving said liquid composition to act onto said surface for a period of time to allow said composition to act, with or without applying mechanical action, and optionally removing said liquid composition, preferably with a cloth or paper towel.

In another preferred embodiment, said method of sanitizing a hard surface includes the step of applying the composition by means of a wipe or pad. The wipe preferably comprises a blend of synthetic and cellulosic fibres for absorption and metering of solution. The load factor, defined as the weight ratio of antimicrobial solution to nonwoven substrate is preferably from about 3× to about 10×. Preferably, the load factor is between 4× and 8×, or from 4.5× to 7.5×, or from 5× to 7×. It is found that higher load factors for the pre-moistened wipes of the invention are preferable since they help increase product mileage on treated surfaces and also reduce the amount of biocidal active and polymer needed to pass the US EPA residual self-sanitizing test.

EXAMPLES

Nonwoven Wipes

A nonwoven roll is first cut into even sized 'wipes' with dimensions of 200 mm×185 mm.

Antibacterial formulations solutions are impregnated into nonwoven substrate 'wipes' at a load factor of 6.6 grams of solution per gram of nonwoven substrate.

Substrate 'A' has a basis weight of 51 grams per square meter (gsm)±3 gsm and is formed as a composite of three layers: two outer scrim layers (7-8 grams per square meter each) comprised of 100% PP and one inner layer, sandwiched between the 2 outer layers, consisting of a blend of cellulose and PP. The overall ratio of PP to cellulose fivers is 65:35.

Substrate 'B' has the same dimensions as substrate 'A', the same basis weight as substrate 'A' (e.g., 51 gsm±3 gsm), and the same architecture as substrate 'A' (e.g., two 7-8 gsm outer layers made of 100% PP and an inner layer consisting of a blend of cellulose and PP. The key difference is that overall weight ratio of PP to cellulose fibres is 80:20

Substrate 'C' is identical to nonwoven substrates 'A' and 'B' except that the overall weight ratio of PP to cellulosic fibres is 40:60.

Substrate 'D' is a single layered wipe. The composition of the substrate is approximately 40% polyester, 40% polypropylene and 20% cellulose.

Aqueous Chemistry Surfactants, Solvents, Biocidal Agents and Polymers

Tween 20=Polyethylene glycol (20) sorbitan monolaurate obtained from Croda International, 100% activity Bio-Soft N1-9=Linear alcohol (C11) ethoxylate, polyoxyethylene (9) from Stepan, 100% activity Dowanol PnB: Propylene glycol n-butyl ether (mixture of isomers) obtained from Dow Chemical, 100% activity.

Ganex P-904 LC: Hydrophobically modified polyvinyl pyrrolidone (butylated) obtained from Ashland Chemical, 100% activity.

CHD=Chlorhexidine diacetate hydrate from Medichem S.A., Spain, 100% activity Bardac 208M=Alkyl ($C_{14}$ 50%, $C_{12}$ 40%, $C_{16}$ 10%) dimethyl benzyl ammonium chloride (32%)+octyl decyl dimethyl ammonium chloride (24%)+dioctyl dimethyl ammonium chloride (9.6%)+didecyl dimethyl ammonium chloride (14.4%) obtained from Lonza, 80% activity.

Carboquat H: Didecyl dimethyl ammonium bicarbonate/carbonate from Lonza, 50% activity.

Bardac 2250=Didecyl dimethyl ammonium chloride from Lonza, 50% activity

Carsoquat CT-429=Cetyl trimethyl ammonium chloride from Lonza, 29% activity

Steol CS-460=Sodium lauryl ether (3) sulfate, from Stepan Corporation, 60% activity Xiameter AFE-1410: Antifoam emulsion obtained from Dow Chemical, 10% activity Chemical Compositions All chemical compositions shown are expressed in terms of raw material active amounts. For example, a composition listed as having 0.25% 'Bardac 2250' comprises 0.25% dodecyl dimethyl ammonium chloride in the formulation, and is made by including 0.50% of the Bardac 2250 raw material. All chemical components are expressed as percentages on a weight basis of active raw material per weight of the total formulation including water.

Examples 1-4

|  | -1- | -2- | -3- | -4- |
|---|---|---|---|---|
| Tween 20 | 0.035 | 0.035 | 0.035 | 0.035 |
| Bio-Soft N1-9 | 0.035 | 0.035 | 0.035 | 0.035 |
| Ganex P-904 LC | 0.50 | 0.50 | 0.50 | — |
| Dowanol PnB | 0.50 | 0.50 | 0.50 | 0.50 |
| CHD | 0.20 | 0.20 | 0.20 | 0.20 |
| Bardac 208M | 0.20 | — | — | — |
| Bardac 2250 | — | 0.20 | — | 0.20 |
| Bardac 4280Z | — | — | 0.20 | — |
| Xiameter AFE | 0.003 | 0.003 | 0.003 | 0.003 |
| Fragrance | 0.05 | 0.05 | 0.05 | 0.05 |
| Water & pH trim: | Remainder | Remainder | Remainder | Remainder |
| Product pH | 6.7 | 6.6 | 6.7 | 6.6 |

Each of the above compositions is made into pre-moistened wipes:

51 gram per square meter nonwoven substrates, 185 mm×200 mm are pre-weighed into pre-labeled 9 inch×12 inch Uline 6 mil zip-lock plastic bags. The plastic bags are unzipped and test solution composition (e.g., −1 through −4) is charged into the bag by means of a disposable 23 ml transfer pipet so as to deliver 6.6 grams of test solution per gram of nonwoven substrate. The bag is then re-sealed and placed on a flat table. By manually pressing on the outside of the zip-lock bag (both sides), the test solution is uniformly distributed throughout the stack of wipes. The bag is then resealed and the residual self-sanitizer test is run several weeks thereafter.

Test Protocol:

Residual activity measurements are performed using a modified version of the Residual Self-Sanitizing Activity on Hard, Non-Porous Surfaces, EPA Protocol #01-1A. Testing is conducted on a 2.5 cm by 2.5 cm area of a glass microscope slide inoculated using the test organism *Enterococcus aerogenes* ATCC 13048. Following complete drying of the inoculum (geometric mean=$2.57 \times 10^7$ CFU/carrier=7.41 log), the impregnated wipe passes over the surface over and back once for a total of 2 passes. The solution left behind from the wipes on the test surface is allowed to visually dry (at least 3 hours) prior to starting the wear cycles. The number of wear cycles is 5, and the number of re-inoculations is 1. The sanitizer test following the 5$^{th}$ wear cycle was performed using a 5-minute exposure time and ambient temperature (~20°). The methodology is illustrated below:

| Day | Procedure |
|---|---|
| 1 | Initial inoculation- hold until dry |
|   | Test substance application- hold overnight |
| 2 | Wear cycle #1 (dry) No hold |
|   | Re-inoculation- hold until dry |
|   | Wear cycle #2 (wet) |
|   | Wear cycle #3 (wet) |
|   | Wear cycle #4 (dry) |
|   | Wear cycle #5 (wet) |
|   | Sanitizer test |

Results—Examples 1-4

| Example | Log kill | Percent reduction | Pass/Fail |
|---|---|---|---|
| 1 | 4.41 | >99.9% | Pass |
| 2 | 3.35 | >99.9% | Pass |
| 3 | 3.05 | >99.9% | Pass |
| 4 | 1.73 | 97.5% | Fail |

Results show the benefit of hydrophobically modified (butylated) PVP. An additional 2.68 log kill benefit is achieved by inclusion of Ganex P-904 LC at 0.5% (compare formula 1 & formula 4). Note that the actual Residual Self-Sanitizing Activity on Hard, Non-Porous Surfaces, EPA Protocol #01-1A is a tougher test with 5 re-inoculation cycles and 12 wear cycles is illustrated below:

| Day | Procedure |
|---|---|
| 1 | Initial inoculation/drying |
|   | Test substance application/drying |
| 2 | Wear cycle #1 (dry) |
|   | Re-inoculation #1- hold until dry |
|   | Wear cycle #2 (wet) |
|   | Re-inoculation #2- hold until dry |
|   | Wear cycle #3 (dry) |
|   | Re-inoculation #3- hold until dry |
|   | Wear cycle #4 (wet) |
|   | Re-inoculation #4- hold until dry |
|   | Wear cycle #5 (dry) |
|   | Re-inoculation #5- hold until dry |
|   | Wear cycle #6 (wet) |
|   | Re-inoculation #6- hold until dry |
| 3 | Wear cycles #7 through #12- hold until dry |
|   | Sanitizer test |

Examples 5-7

In these examples, a single chemical composition is impregnated onto four different nonwoven substrates and evaluated using the full EPA Protocol #01-1A protocol (e.g., 6 re-inoculation cycles & 12 wear cycles) described above. The test is run vs. *Enterococcus aerogenes* ATCC 13048.

Composition #5: 0.07% Tween 20+0.07% C11 EO9+ 0.75% Ganex P-904 LC+0.25% CHD+0.5% Bardac 208M+ 0.003% Xiameter AFE-1410, pH adjusted to 6.6. This composition is charged onto nonwoven substrates 'A', 'B' and 'C' using the load factor (6.6x) and application procedure detailed for examples 1-4. Following complete drying of the inoculum (geometric mean=1.66×10$^7$ CFU/carrier=7.22 log), the impregnated wipe passes over the surface over and back once for a total of 2 passes.

Results—Examples 5-7

| Example | Solution & Substrate | Log kill | Percent reduction | Result |
|---|---|---|---|---|
| 5 | #5 & 'A' | 3.89 | >99.9% | Pass |
| 6 | # 5 & 'B' | 4.00 | >99.9% | Pass |
| 7 | # 5 & 'C' | 3.77 | >99.9% | Pass |

It is worth noting positive results for solution #5 even when embedded in a nonwoven substrate comprising 60% cellulosic fibres. Commercial processing of cellulosic is known to create negatively charged sites on the web, and these will ion-pair and bind with cationic actives such as chlorhexidine salts, biguanide compounds and quaternary ammonium biocides. Wipe binding of quaternary ammonium compound and chlorhexidine diacetate respectively was analytically measured below:

| Example | Solution Quat & CHD | Wipe Expressed Quat & CHD | Percent Quat & CHD Lost to Wipe Binding |
|---|---|---|---|
| 5 | 0.246% & 0.243% | 0.234% & 0.231% | 5% & 5% |
| 6 | 0.246% & 0.243% | 0.204% & 0.199% | 17% & 18% |
| 7 | 0.246% & 0.243% | 0.173% & 0.176% | 30% & 27% |

Example 7 illustrates the robustness of the hydrophobically modified polyvinyl pyrrolidone of the invention in providing residual sanitizer benefits vs. *Enterococcus aerogenes* ATCC 13048 despite the loss of 25-30% cidal active due to substrate binding, the formulation still passes the RSS test.

Examples 8-10

Nonwoven substrate 'D' is impregnated with composition #5 at a load factor of 6.6x. In example 8 & 10, the substrates are packaged as flat packs in Uline zip-lock bags following the same procedure outlined above for examples 1-7. In example 9, the dry wipes are formed as a z-folded 35 wipe-count roll inside a commercial canister, then lotioned with composition #5 at a 6.6x load factor. For RSS testing purposes, the first four wipes from the canister are pulled out and discarded, and testing is then conducted with the next nonwoven substrate dispensed through the orifice of the canister.

In example 8 & 9, the test organism is *Enterococcus aerogenes* ATCC 13048. In example 10, the test organism is Influenza A virus (H1N1).

Results—Examples 8-10

| Example | Solution & Substrate | Log kill | Percent reduction | Result |
|---|---|---|---|---|
| 8 | #5 & 'D' | 4.30 | >99.9% | Pass |
| 9 | # 5 & 'D' | 4.12 | >99.9% | Pass |
| 10 | # 5 & 'D' | ≥3.14 | >99.9% | Pass |

Examples 8-10 illustrate the versatility of the hydrophobically modified polyvinylpyrrolidone polymer of the invention for passing RSS test. Changing the architecture of the nonwoven substrate of example 5-7 has no impact on the result, and neither does making the wipes in canisters as opposed to flat packs. Finally, example 10 illustrates the versatility of the polymer of the invention in promoting residual sanitization against viruses as well as bacteria.

Examples 11-14

In examples 11-13, composition is impregnated into non-woven substrate 'D' at a load factor of 6.6× and evaluated using the full EPA Protocol #01-1A protocol (e.g., 6 re-inoculation cycles & 12 wear cycles) described above. The tests are run vs. *Enterococcus aerogenes* ATCC 13048 (examples 11-13) and *Staphylococcus aureus* ATCC 6538 (example 11 only). Example 14 is evaluated as a spray product (not a wipe) vs. *Enterococcus aerogenes* ATCC 13048.

|  | -11- | -12- | -13- | -14- |
|---|---|---|---|---|
| Tween 20 | 0.07 | — | — | 0.07 |
| Bio-Soft N1-9 | 0.07 | 0.14 | 0.14 | 0.07 |
| Ganex P-904 LC | 0.50 | 0.75 | 0.75 | 0.35 |
| Ethanol | 0.50 | 0.50 | 0.50 | 0.50 |
| CHD | 0.20 | 0.40 | 0.40 | 0.30 |
| Carboquat H | — | — | — | 0.05 |
| Carsoquat CT-429 | 0.02 | — | — | — |
| Steol CS-460 | — | 0.05 | — | 0.20 |
| Gluconic Acid | — | — | — | 0.02 |
| Xiameter AFE | 0.003 | — | — | 0.003 |
| Fragrance | 0.04 | 0.07 | 0.03 | 0.03 |
| Water & pH trim: | Remainder | Remainder | Remainder | Remainder |
| Solution pH | 6.5 | 6.9 | 7.0 | 6.6 |

*Cetyl trimethyl ammonium chloride, 29% active from Lonza
**Sodium lauryl ether (3) sulfate, 60% active from Stepan Corporation Results—Examples 11-14

| Example | Solution & Substrate | Organism | Log kill | Result |
|---|---|---|---|---|
| 11 | #11 & 'D' | E. aerogenes | >99.9% | Pass |
| 11 | # 11 & 'D' | S. aureus | >99.9% | Pass |
| 12 | # 12 & 'D' | E. aerogenes | >99.9% | Pass |
| 13 | # 13 & 'D' | E. aerogenes | >99.9% | Pass |
| 14 | #14 Spray | E. aerogenes | >99.9% | Pass |

Results show the capability to pass the residual self-sanitizer test (RSS), EPA Protocol #01-1A protocol vs. Gram (−) and Gram (+) bacteria; results also show that ability to pass as a wipe or a spray as well as the ability pass the test with chlorhexidine diacetate as the only germicidally active species.

Shine Testing:

The shine test is done using black glossy ceramic tiles (Black Glossy Sphinx ceramic tiles 20×25 cm, Ref H07300, available at Carobati, Boomsesteenweg 36, 2630 Aartselaar www.carobati.be). The tiles are then sprayed (3-3 full sprays per tile) with Windex glass cleaner solution, the solution is spread (paper towel) to ensure complete coverage of the tile, and then immediately wiped off by means of a squeegee. The tiles are then sprayed with isopropanol solution (70%) ensuring again complete coverage of the tile prior to removal of the isopropanol solution by means of squeegee. The tile is then allowed to completely air dry at ambient temperature (20-25° C.).

Shine measurements of clean and product-treated tiles are performed using a pre-calibrated Rhopoint IQ 20/60/85 Gloss Haze Meter obtained from Rhopoint Instruments, United Kingdom. Nine readings across each full tile are made and averaged. The results for 20°, 60° gloss measurements and specular reflectance (Rspec) are recorded. The difference between the respective 20° and 60° and Rspec measurements after surface treatment and before surface treatment (e.g., Δ 20° Gloss, Δ 60° Gloss & Δ Rspec vs. clean tile readings) is used to quantify the degree to which the compositions tested modify the shine of the tile. Small reading differences suggest that the product treatment has had only a negligible effect on the natural gloss of the tile being tested. In some cases, it has been found that the alkylated polyvinylpyrrolidone of the invention provides higher gloss and specular reflectance readings, meaning that it enhances tile gloss. Further, the methodology is used to quantify the effect that the alkylated polyvinylpyrrolidone polymer of the invention can have on tile shine.

The pre-moistened wipes are wrapped around a 1 kg block (10.5 cm base×5.5 cm height*6.5 cm width) that is manually pushed across so as to cover the entire tile area using 4 side-to-side passes followed by 4 up-and-down passes. An average of 0.6±0.1 grams are expressed from the pre-moistened wipes. The wet tile is allowed to completely dry, gloss measurement readings are taken from 9 points covering the tile, and averaged together.

Glossmeter Results—Compositions of Examples 1~4

| Example | Δ 20° Gloss | Δ 60° Gloss | Δ Rspec |
|---|---|---|---|
| 1 | −2.7 | −2.4 | −2.0 |
| 2 | −0.2 | −2.2 | −2.1 |
| 3 | −0.4 | −1.5 | +1.9 |
| 4 | −22.6 | −19.5 | −18.9 |

Example #4, which lacks the alkylated polymer of the invention shows significant losses in glosses upon treatment with a composition that lacks the polymer of the invention. By contrast, examples #1, #2, #3, all of which contain alkylated polyvinylpyrrolidone, show only small effects in gloss as a result of the pre-moistened wipe treatment.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hard surface cleaning antimicrobial composition comprising:
   from 0.05 to 2 wt. % butylated polyvinylpyrrolidone polymer; and
   from 0.05 to 2 wt. % biocidal agent selected from the group consisting of quaternary ammonium compounds, chlorohexidine diacetate and mixtures thereof;
   from 0.01 to 1 wt. % non-ionic surfactant; and
   from 0.05 to 5 wt. % solvent selected from the group consisting of C2 to C4 alcohols, glycol ethers, and mixtures thereof, wherein:
      the butylated polyvinylpyrrolidone polymer has a molecular weight of from 5,000 to 40,000 g/mol, wherein the hard surface cleaning antimicrobial composition comprises greater than 80 wt. % water.

2. The hard surface cleaning antimicrobial composition according to claim 1, wherein the quaternary ammonium compound is selected from the group consisting of dodecyl dimethyl ammonium bicarbonate/carbonate, didecyl dimethyl ammonium chloride, C12-C18 dimethyl benzyl ammonium chloride, C12-C18 dimethyl ethylbenzyl ammonium chloride, and mixtures thereof.

3. The hard surface cleaning antimicrobial composition according to claim 1, further comprising a nonionic surfactant.

4. The hard surface cleaning antimicrobial composition according to claim 1, further comprising a solvent selected from the group consisting of C2 to C4 alcohols, glycol ethers, and mixtures thereof.

5. The hard surface cleaning antimicrobial composition according to claim 1, wherein the hard surface cleaning antimicrobial composition imparts residual sanitization.

6. The hard surface cleaning composition according to claim 1, comprising:
   a) from 0.05% to 2% by weight of the hard surface cleaning antimicrobial composition of the butylated polyvinylpyrrolidone polymer;
   b) from 0.05% to 2% by weight of the hard surface cleaning antimicrobial composition of the chlorohexidine diacetate;
   c) from 0.05% to 2% by weight of the hard surface cleaning antimicrobial composition of a quaternary ammonium compound;
   d) from 0.05% to 2% by weight of the hard surface cleaning antimicrobial composition of a non-ionic surfactant; and
   e) from 0.05% to 50% by weight of the hard surface cleaning antimicrobial composition of a glycol ether.

7. An article treated with the hard surface cleaning antimicrobial composition according to claim 1, wherein the article is in the form of a disposable or partially reusable substrate comprising one or more nonwoven layers and the substrate has a load factor of from about 3 times to about 10 times of composition per gram of nonwoven substrate.

8. A canister comprising the article according to claim 7.

9. A method for sanitizing a surface, providing residual self-sanitizing efficacy and shine, comprising the steps of wiping the surface with an article according to claim 8, wherein the surface comprises at least one of the following materials: ceramic, vinyl, no-wax vinyl, linoleum, melamine, glass, steel, kitchen work surfaces, plastic, plastified wood, metal, painted surfaces, varnished surfaces.

10. The hard surface cleaning antimicrobial composition according to claim 1, wherein the biocidal agent comprises chlorohexidine diacetate, and wherein the hard surface cleaning antimicrobial composition comprises from 0.20% to 1.0% of the biocidal agent by weight of the hard surface cleaning antimicrobial composition.

11. A canister comprising a plurality of antimicrobial articles for cleaning hard surfaces, each of the plurality of articles being treated with a composition comprising:
   (a) butylated polyvinylpyrrolidone polymer; and
   (b) a biocidal agent selected from the group consisting of quaternary ammonium compounds, chlorohexidine diacetate and mixtures thereof, wherein the butylated polyvinylpyrrolidone polymer has a molecular weight of from 5,000 to 40,000 g/mol, wherein the hard surface cleaning antimicrobial composition comprises greater than 80 wt. % water wherein a pH of the hard surface cleaning antimicrobial composition is from 5 to 8.

12. The plurality of antimicrobial articles for cleaning hard surfaces of claim 11, wherein each of the plurality of articles comprises a plurality of synthetic fibers and a plurality of cellulose fibers.

13. The hard surface cleaning antimicrobial composition according to claim 1, wherein a pH of the hard surface cleaning antimicrobial composition is from 5 to 8.

* * * * *